United States Patent
Muller et al.

(10) Patent No.: US 9,719,921 B2
(45) Date of Patent: Aug. 1, 2017

(54) SOLID BODY

(71) Applicant: Endress + Hauser Conducta Gesellschaft für Mess- und Regeltechnik mbH + Co. KG, Gerlingen (DE)

(72) Inventors: Andreas Muller, Ostfildern (DE); Matthias Grossmann, Vaihingen-Enz (DE); Thilo Kratschmer, Stuttgart (DE)

(73) Assignee: Endress+Hauser Conducta GmbH+Co. KG, Gerlingen (DE)

(*) Notice: Subject to any disclaimer, the term of this patent is extended or adjusted under 35 U.S.C. 154(b) by 416 days.

(21) Appl. No.: 13/904,690

(22) Filed: May 29, 2013

(65) Prior Publication Data
US 2013/0321809 A1    Dec. 5, 2013

(30) Foreign Application Priority Data

May 31, 2012  (DE) .................. 10 2012 104 721

(51) Int. Cl.
*G01N 21/53* (2006.01)
*G01N 21/47* (2006.01)

(52) U.S. Cl.
CPC .......... *G01N 21/53* (2013.01); *G01N 21/4785* (2013.01)

(58) Field of Classification Search
CPC ....... G01N 21/4785; G01N 21/53; G01J 1/10; G01J 1/02
See application file for complete search history.

(56) References Cited

U.S. PATENT DOCUMENTS

| | | | |
|---|---|---|---|
| 5,741,441 A * | 4/1998 | Watts et al. ................. | 252/408.1 |
| 5,757,481 A * | 5/1998 | O'Brien et al. ........... | 356/239.1 |
| 7,659,980 B1 * | 2/2010 | Mitchell et al. ............. | 356/339 |
| 7,843,560 B2 * | 11/2010 | Harner et al. ............. | 356/243.2 |
| 2009/0059218 A1 | 3/2009 | Harner | |
| 2010/0235133 A1 | 9/2010 | Palumbo | |

FOREIGN PATENT DOCUMENTS

| | | |
|---|---|---|
| DE | 2741914 | 4/1978 |
| GB | 1595207 | 8/1981 |
| JP | 4919003 B2 | 12/2007 |

OTHER PUBLICATIONS

German Search Report, Munich, Jan. 8, 2013.

* cited by examiner

*Primary Examiner* — Rebecca C Bryant
(74) *Attorney, Agent, or Firm* — Mark A. Logan; PatServe

(57) ABSTRACT

A solid body for adjusting, calibrating and/or function checking of a turbidity sensor, which works with electromagnetic waves, especially light, of at least a first wavelength, and wherein the solid body is transparent at least for the light of the first wavelength, characterized in that at least a first region is provided in the solid body, where at least incident light of the first wavelength is scattered. The scattered light is a measure for turbidity.

9 Claims, 3 Drawing Sheets

SOLID BODY

TECHNICAL FIELD

The invention relates to a solid body for adjusting, calibrating and/or function checking of a turbidity sensor.

BACKGROUND DISCUSSION

Turbidity measurements in the sense of this invention are performed by means of a turbidity sensor especially in fresh water, water for industrial use and waste water as well as gases. Furthermore, the invention relates to measurements of similar process variables, such as solids content, and sludge, or mud, level. Measuring devices suitable for determining the corresponding process variables are produced and sold by the group of firms, Endress+Hauser, in a large number of variants, for example, under the designation "Turbimax CUS51D" and "Turbimax W CUS65".

Usually, the sensors are arranged in a sensor body, and the determination of the process variable occurs optically. In such case, electromagnetic waves of a certain wavelength are sent from at least one transmitting unit, scattered by the medium to be measured and received by a receiving unit. The wavelengths of the electromagnetic waves of the optical components lie typically in the near infrared, for example, at 860 nm. Especially in the American market, however, also white light sources are used.

The transmitters are, most often, narrow band radiators, e.g. a light-emitting diode (LED). In such case, the LED is used for producing light lying in a suitable wavelength range. Applied as a receiver can be a corresponding photodiode, which produces from the received light a receiver signal, for example, a photocurrent or a photovoltage.

In order to make turbidity measurements comparable, turbidity standard liquids are applied, such as, for example, formazine. The most common turbidity units are FAU (Formazine Attenuation Unit), FNU (Formazine Nephelometric Unit), FTU (Formazine Turbidity Unit), NTU (Nephelometric Turbidity Unit), TU/F (Turbidity Unit/Formazine), EBC (European Brewery Convention) and ASBC (American Society of Brewing Chemists).

As a rule, turbidity sensors are calibrated with the standard, formazine.

Formazine is a mixture of hydrazine sulfate and urotropine. Production of formazine must be done very carefully, in order to achieve reproducible results.

Formazine has only a very low storability. Especially in the case of low turbidity values, the storability amounts to only a few hours.

Moreover, formazine may be mutagenic and carcinogenic.

An alternative to formazine is a reference material in the form of a solid body. Solid body standards can, in contrast, be stored for longer periods of time, to the extent that materials, which age, are avoided. They are additionally less questionable as regards handling.

Solid body standards have, until now, been made either of materials, which scatter incident light (e.g. turbid synthetic materials) or of materials, in the case of which synthetically introduced structures are responsible for the light scattering. The latter have, on the one hand, the advantage that specific, different turbidity values can be implemented and, on the other hand, that the provided structures can be limited locally to certain regions of the solid. This has until now been implemented exclusively by means of a glass body, in the case of which small foreign particles with an index of refraction different from the glass are introduced by doping. This method is like scattering the light on suspended particles in liquids and is thus suitable as a secondary standard. The process of doping the glass is, however, relatively complicated and, thus, very expensive.

SUMMARY OF THE INVENTION

An object of the invention is, therefore, to provide a cost effective solution for imitating the light scattering on particles suspended in liquids and gases.

The object is achieved by a solid body for a turbidity sensor, which works with electromagnetic waves, especially light, of at least a first wavelength, and wherein the solid body is transparent at least for the light of the first wavelength. Provided in the solid body is at least a first region, where at least incident light of the first wavelength is scattered, wherein the scattered light is a measure for turbidity.

In an advantageous embodiment, at least one energy input into the at least first region leads in the solid body to at least one microcrack, wherein the at least one microcrack has dimensions of less than 1000 µm, especially less than 500 µm, especially less than 250 µm. A microcrack in the sense of this invention is to be considered as a structural change in the solid body, i.e. as a defined zone, which differs from its environment.

The energy input enables that the at least one microcrack is introduced in a precise manner into the solid body.

In a preferred form of embodiment, a multiplicity of microcracks with a defined microcrack density is provided, wherein the microcrack density is a measure for turbidity, wherein "microcrack density" in the sense of this invention depends on the number of microcracks, the shape of the microcracks, the size of the microcracks and on the separation of the microcracks from one another. By varying one of the parameters, number, shape, size and/or separation of the microcracks from one another, the microcrack density can be changed.

Advantageously, the microcracks are uniformly distributed, especially in the case when the incident light is not uniformly distributed. If the microcracks are uniformly distributed, the measured turbidity does not change, in case the light distribution changes, although, if the light distribution is non-uniform, then the measured turbidity does change.

A special advantage is achieved when the microcrack density is so embodied that the measure for turbidity is referenced to a turbidity standard liquid, especially such that the measure for turbidity can be expressed in at least one of the turbidity units FAU, FNU, FTU, NTU, EBC, TEF, ASBC or TU/F. If the microcrack density is referenced to a turbidity standard liquid, the solid body can be used as a secondary standard.

In an embodiment, the turbidity standard liquid is formazine.

Preferably, the energy input is effected by laser. In this way, the microcracks can be introduced simply, precisely and cost effectively into the solid body.

Preferably, the solid body comprises one of the group of materials, glass, sapphire, diamond, polymethylmethacrylate and polycarbonate. These materials have in general the properties that they are transparent for the light of the first wavelength and that microcracks can be introduced into the first region, so that light can be scattered.

The solid body is embodied in the form of any cuboid, for example, in the form of a cube. Other options for forms include pyramids, spheres, etc. Typical dimensions of the solid bodies lie in the range from several millimeters to a number of centimeters.

In an advantageous further development, there are provided in the solid body a plurality of regions, which are so embodied that, in each case, another measure for turbidity is provided. Since, in practice, usually a number of points will be adjusted, calibrated or checked, such can be done for a sensor using a single solid body having a plurality of regions.

The object is furthermore achieved by a turbidity sensor, in the case of which the solid body is so positioned on the turbidity sensor that the turbidity sensor is adjusted, calibrated or subjected to function checking in one of the methods, back scatter light, 90°-scattered light, forwards scatter light or transmitted light.

Moreover, the object is achieved by a method, in the case of which the solid body is so positioned on the turbidity sensor that the turbidity sensor is adjusted, calibrated or subjected to function checking in one of the methods, back scatter light, 90°-scattered light, forwards scatter light or transmitted light.

BRIEF DESCRIPTION OF THE DRAWINGS

The invention will now be explained in greater detail based on the appended drawing, the figures of which show as follows:

FIG. 1b is a side view of the solid body as produced, for example, with the step of FIG. 1a;

Figure 1A:
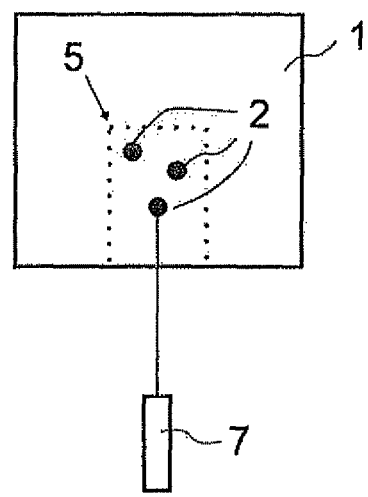
FIG. 1a is in side view, a schematic representation of a step in the manufacture of the solid body.

In the figures, equal features are provided with equal reference characters.

DETAILED DISCUSSION IN CONJUNCTION WITH THE DRAWINGS

The solid body of the invention is given the reference character 1. Solid body 1 is produced from one of the group of materials, glass, sapphire, diamond, polymethylmethacrylate or polycarbonate and has dimensions in the centimeter range, for example, the solid body 1 is embodied as a cube with an edge length of 4 cm. A cube has the advantage of easy handling. In general, however, options include a (any) cuboid, pyramid, sphere etc. Size is, in such case, not critical. Important is that the size be suitable for the calibration of a turbidity sensor (see below).

FIG. 1a shows the critical manufacturing step schematically. A laser 7 radiates highly energetic laser light onto the solid body 1, more exactly into a first region 5. In such case, lenses, mirrors and possibly other optical tools and methods are used, in order to focus the laser beam on a point in the region 5. In a variant, an option is to use a number of lasers 7, which are focussed on a point, in order to produce a microcrack 2 there (see below).

The first region 5 takes up a portion of the solid body 1. An option is that the first region 5 comprises a number of centimeters, and, in the maximum case, the first region 5 makes up the complete solid body 1. Since the laser 7 produces microcracks 2 of several hundred micrometers in the first region 5 (see below), the first region can also only be a few millimeters.

In the focus, the spatial and time energy density of the laser beam is so high that, by ionizing and plasma forming, the solid body 1 is thermally destroyed and crystallized there (with accompanying crack formation, melting and evaporation), while the broad beam therebefore and therebehind the focus damages neither the two solid surfaces nor the lenses. The resulting microcracks are given the reference character 2.

The laser 7 or the solid body 1 are moved in the x-, y- and z-directions, in order to obtain microcracks 2 at different spatial locations.

A microcrack 2 in the sense of this invention is to be considered as a structural change in the solid body, i.e. as a defined zone, which differs from its environment. In such case, the form of the microcracks 2 can be selected as a function of requirement. Typical forms are rice grain like or spherically shaped structures with dimensions of a few hundred micrometers, with typical values being less than 1000 µm, especially less than 500 µm, especially less than 250 µm.

Figure 1B:
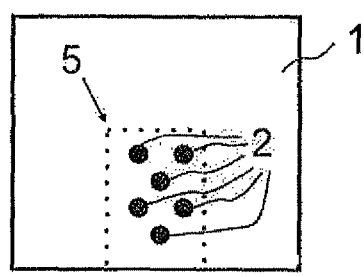

FIG. 1b shows the result. Located in the first region 5 is a regular pattern of microcracks 2. Of course, also irregular structures can be used.

The microcracks 2, in principle, simulate particles in a liquid or a gas. If light falls on the microcracks 2, the light is scattered. The type and amount of the scattering is a measure for turbidity. Thus, associated with each pattern is a certain turbidity value, wherein the microcrack density (see below) determines the scattering and, therewith, the turbidity. The turbidity value is based on one of the units, FAU, FNU, FTU, NTU, EBC, ASBC or TU/F. Possible are turbidity values of almost 0 FNU (very clear water) up to several hundred, especially up to several thousand FNU.

This turbidity value is compared with a liquid standard, for example, formazine, so that the laser treated, solid body can serve as a secondary standard.

If the microcracks 2 are positioned quite close to one another, a large turbidity is simulated; there is a high microcrack density. If the microcracks 2 are positioned farther away from one another, a low turbidity is simulated; there is a small microcrack density.

Besides the separation of the microcracks 2 from one another also shape, size and number of microcracks 2 have an influence on the microcrack density, wherein the microcrack density, as already mentioned, is a measure for turbidity, i.e. if at least one of the four parameters (number, shape, size, separation) is changed, this has an influence on the microcrack density and, thus, on the simulated turbidity. The shape, size, separation and number of microcracks 2 can also be so embodied that the most varied of media, particle, sludge or mud types, bacteria, etc. can be simulated.

Figure 2A:
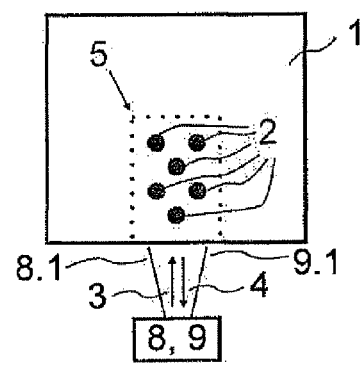
FIG. 2a-FIG. 2c are side views of the solid body illustrating three measuring methods.
Figure 2B:
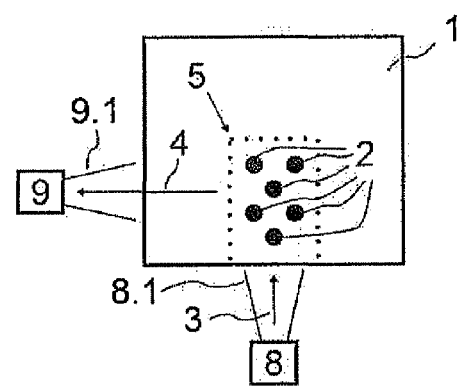
Figure 2C:
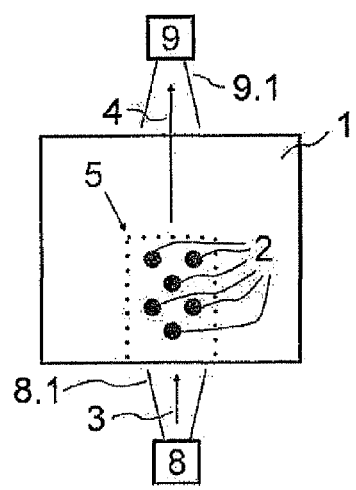

FIGS. 2a-c illustrate application of the solid body 1. A turbidity measuring device includes at least one transmitting unit 8 and a receiving unit 9. For calibration of the turbidity measuring device, the transmitting unit 8 sends light, for example, with a wavelength of 860 nm, in a certain aperture angle 8.1 toward the solid body 1, especially toward the region 5. In a variant of the invention, a white light source is used. The solid body 1 is essentially transparent for the radiated light 3, but, in the region 5, the light is scattered and the scattered light 4 reaches receiving unit 9, which receives the light in a certain aperture angle 9.1.

Since there is, as above described, a certain turbidity value associated with the solid body 1, an adjusting, calibration and/or function checking of the turbidity sensor can occur.

FIGS. 2a-c show different measuring methods.

FIG. 2a illustrates the back scatter method, wherein the back scattered light is measured. In such case, the incident light 3 and the scattered light 4 are represented by arrows. FIG. 2a shows transmitting unit 8 and receiving unit 9 as a single unit. Of course, also the use of separated units is an option. The measuring of the back scattering can occur at different angles.

FIG. 2b shows the 90°-scattered light method, in the case of which the scattered light 4 is measured, which is scattered 90° to the radiated light 3.

FIG. 2c shows the transmitted light method or the forwards scatter method, in the case of which the transmitted light or the forwards scattering is measured. The measuring of the forwards scattering can occur at different angles. Thus, for instance, the receiving unit 9 does not have to lie in the same plane as the transmitting unit 8.

Figure 3:
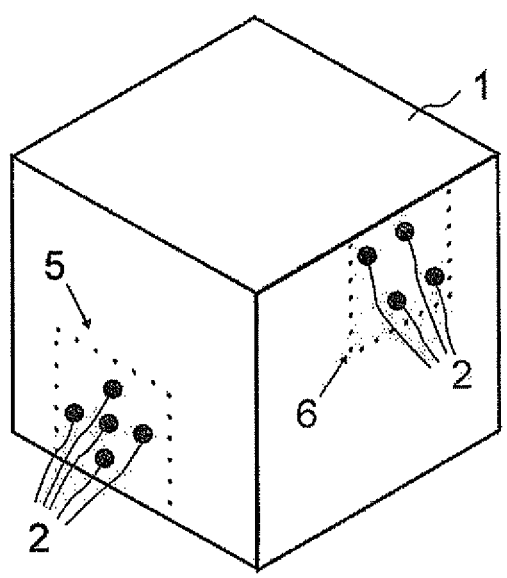
FIG. 3 is an isometric view of a preferred embodiment of the solid body.

FIG. 3 shows an isometric view of the solid body 1 in a preferred embodiment. In such case, supplementally to the first region 5, a second region 6 is provided. In the second region 6, another structure of the microcracks 2 is provided. This is indicated in FIG. 3 with the different number of microcracks 2. In general, however, also other patterns, sizes, forms, etc. can be used in the second region 6. Thus, with one solid body 1, a number of different turbidity values can be simulated. In such case, only the position or orientation of solid body 1 needs to be changed. In FIG. 3, the regions 5 and 6 do not meet. Nevertheless, it is naturally possible and for certain applications also sensible to have the regions 5 and 6 overlap. Of course, also more than only two different regions are possible. Thus, an option is, for instance, that a first region 5 overlaps a second region 6, so that a third region forms in the overlap zone. Moreover, a fourth and a fifth region can result, when one rotates, or shifts, the solid body 1, the transmitting unit 8 and/or the receiving unit 9, so that the incident light 3 strikes the overlap zone from another side.

The invention claimed is:

1. A method for adjusting, calibrating or function checking of a turbidity sensor, comprising the steps:
   providing a solid body that is transparent for light of at least a first wavelength, wherein the solid body contains a first region, the first region containing plurality of microcracks, and wherein the first region is assigned a turbidity value;
   providing a turbidity sensor comprising a light transmitting unit and at least one light receiving unit;
   positioning the solid body on the turbidity sensor;
   transmitting light of the first wavelength from the light transmitting unit into the first region of the solid body, whereby the light is scattered by the microcracks in the first region;
   receiving with at least one light receiving unit light scattered by the microcracks in the first region;
   measuring a turbidity value from the received light;
   comparing the measured turbidity value with the assigned turbidity value of the first region; and
   adjusting, calibrating, or function testing the turbidity sensor based on comparing the measured turbidity value with the assigned turbidity value.

2. A method for manufacturing a solid body for calibrating a turbidity sensor, comprising the steps:
   providing a solid body which is transparent for light of at least a first wavelength;
   focusing a laser into a first region of the solid body at a focal point;
   ionizing and crystalizing the solid body at or near the focal point thereby forming a microcrack;
   moving the focal point of the laser to a different point in the first region;
   repeating the focusing, microcrack forming, and moving steps at different focal points until a desired microcrack density is generated;
   measuring a turbidity value of the first region with a turbidity-measuring apparatus; and
   assigning the turbidity value to the first region.

3. The method for manufacturing a solid body for calibrating a turbidity sensor as claimed in claim 2, the method further comprising the steps:
   focusing the laser into a second region of the solid body at a focal point;
   ionizing and crystalizing the solid body at or near the focal point in the second region thereby forming a microcrack;
   moving the focal point of the laser to a different point in the second region;
   repeating the focusing, microcrack forming, and moving steps at different focal points until a desired microcrack density is generated;
   measuring a turbidity value of the second region with the turbidity-measuring apparatus; and
   assigning the turbidity value to the second region.

4. The method for manufacturing a solid body as claimed in claim 2, wherein the solid body comprises one of the group of materials: glass, sapphire, diamond, polymethylmethacrylate, and polycarbonate.

5. The method for manufacturing a solid body as claimed in claim 2, wherein at least one microcrack has dimensions of less than 1000 μm.

6. The method for manufacturing a solid body as claimed in claim 2, wherein the microcrack density depends on the number, shape, size, and separation of the microcracks from one another and the microcrack density effects a scattering of incident light and is a measure for turbidity.

7. The method for manufacturing a solid body as claimed in claim 2, wherein the microcracks are uniformly distributed.

8. The method for manufacturing a solid body as claimed in claim 2, wherein the microcrack density is so embodied that the measure for turbidity is referenced to a turbidity standard liquid, such that the measure for turbidity can be expressed in at least one of the following turbidity units, FAU, FNU, FTU, NTU, EBC, TEF, ASBC and TU/F.

9. The method for manufacturing a solid body as claimed in claim 8, wherein the turbidity standard liquid is formazine.

* * * * *